(12) United States Patent
Dewaele

(10) Patent No.: US 7,065,235 B2
(45) Date of Patent: Jun. 20, 2006

(54) RADIOGRAPHIC SCORING METHOD

(75) Inventor: Piet Dewaele, Berchem (BE)

(73) Assignee: AGFA-GEVAERT, Mortsel (BE)

( * ) Notice: Subject to any disclaimer, the term of this patent is extended or adjusted under 35 U.S.C. 154(b) by 604 days.

(21) Appl. No.: 10/237,311

(22) Filed: Sep. 9, 2002

(65) Prior Publication Data

US 2003/0053673 A1   Mar. 20, 2003

(30) Foreign Application Priority Data

Sep. 18, 2001   (EP) ................... 01000470

(51) Int. Cl.
*G06K 9/00* (2006.01)
(52) U.S. Cl. .................................... 382/132
(58) Field of Classification Search ............. None
See application file for complete search history.

(56) References Cited

U.S. PATENT DOCUMENTS

| | | | |
|---|---|---|---|
| 4,437,161 A * | 3/1984 | Anderson | 600/425 |
| 4,791,934 A * | 12/1988 | Brunnett | 600/429 |
| 5,740,266 A * | 4/1998 | Weiss et al. | 382/128 |
| 5,839,438 A | 11/1998 | Graettinger et al. | |

FOREIGN PATENT DOCUMENTS

| | | |
|---|---|---|
| EP | 01 00 0470 | 4/2002 |
| WO | WO 00/33252 | 6/2000 |

OTHER PUBLICATIONS

"Finding-Specific Display Presets for Computed Radiography Soft- Copy Reading", Katherine P. Andriole et al., Journal of Digital Imaging, vol. 12, No. 2, May 1999, pp. 3-5.

"A Digital Hand Atlas for Bone Age Assessment of Children—An Application of PACS Database", H.K. Huang et al., SPIE vol. 3662, Feb. 1999, pp. 178-184.

* cited by examiner

*Primary Examiner*—Bhavesh M. Mehta
*Assistant Examiner*—Ashutosh Upreti
(74) *Attorney, Agent, or Firm*—John A. Merecki; Robert A. Sabourin

(57) ABSTRACT

In a method for radiographic scoring of a radiographic image at least one region of interest is determined. Each of the determined regions of interest is displayed in close proximity to a number of reference stages each having an associated score. For each region of interest a reference stage image best matching the displayed region of interest is selected and the score number associated with the selected reference stage image is associated with the region of interest. Score numbers retained for each of the regions of interest are combined to form the score number of the radiographic image.

22 Claims, 8 Drawing Sheets

| stage | reference images | | processed ROI(s) | | sketch skeletal site of ROI | textual description + tickoff box static ROI display | |
|---|---|---|---|---|---|---|---|
| a | $R_{a1}$ | $R_{a2}$ | $ROI_{a1}$ | $ROI_{a2}$ | $S_a$ | Descriptive feature(s) stage a | ☐ |
| b | $R_{b1}$ | $R_{b2}$ | $ROI_{b1}$ | $ROI_{b2}$ | $S_b$ | Descriptive feature(s) stage b | ☐ |
| c | $R_{c1}$ | $R_{c2}$ | $ROI_{c1}$ | $ROI_{c2}$ | $S_c$ | Descriptive feature(s) stage c | ☑ |
| d | $R_{d1}$ | $R_{d2}$ | $ROI_{d1}$ | $ROI_{d2}$ | $S_d$ | Descriptive feature(s) stage d | ☐ |
| e | $R_{e1}$ | $R_{e2}$ | $ROI_{e1}$ | $ROI_{e2}$ | $S_e$ | Descriptive feature(s) stage e | ☐ |
| f | $R_{f1}$ | $R_{f2}$ | $ROI_{f1}$ | $ROI_{f2}$ | $S_f$ | Descriptive feature(s) stage f | ☐ |
| g | $R_{g1}$ | $R_{g2}$ | $ROI_{g1}$ | $ROI_{g2}$ | $S_g$ | Descriptive feature(s) stage g | ☐ |
| h | $R_{h1}$ | $R_{h2}$ | $ROI_{h1}$ | $ROI_{h2}$ | $S_h$ | Descriptive feature(s) stage h | ☐ |

FIG. 6

RADIOGRAPHIC SCORING METHOD

FIELD OF THE INVENTION

The present invention relates to computer-assisted radiological scoring of radiographic images.

BACKGROUND OF THE INVENTION

In radiological practice, radiographic images are used for a variety of diagnostic purposes. Radiographs can be captured to detect and identify lesions, to diagnose an underlying pathology from radiological manifestations, to assess the existence and extent of a fracture etc.

There exist also a domain of specialized radiological examination procedures, which cannot be classified into any of the enumerated tasks, which is the field of radiological scoring.

In radiographic scoring methods, the radiographer or clinician already knows the pathology but wishes to assess the degree of severity of the disease or the developmental stage of the patient.

Several scoring methods exist in the state of the art. All scoring methods have the following specific characteristics in common:

(1) a number of pre-determined anatomical sites on a radiograph is examined; the number of anatomical sites being constant for a given method;

(2) the specific appearance of the anatomical site is rated against a number of reference pictures, each reference picture corresponding to a developmental or pathological stage, and the rating results in a stage being assigned; the number of reference stages being constant for the given anatomical site;

(3) each stage has an associated numerical score, the value of which in general differs according to the stage and the skeletal site;

(4) all scores are totaled and translated into a clinically useful index.

Although rating refers to the process of assigning a stage to an anatomical site and scoring refers to the attribution of a value to the stage, we will call both processes 'scoring' in the sequel.

Radiological scoring methods, which adhere to the aforementioned principles, are e.g. bone age determination (also known as skeletal maturity assessment), rheumatoid arthritis scoring, osteo-arthritis scoring, ankylosing spondylitis scoring, and osteoporosis assessment.

In the following scoring methods applied to different applications will be explained.

A first example of an application wherein radiographic scoring is used, is skeletal maturity assessment, a procedure frequently performed in paediatric radiology.

Biologically, it is desirable to assess the maturity of the whole skeleton, but because of several practical difficulties such as the time needed for the assessment of so many bones, the expense of radiographic film, the risk of excessive radiation exposure etc. a specific area is chosen for the assessment of skeletal maturity.

An area of the human skeleton, which has received considerable attention as a source of clinically relevant maturity indicator, is the hand-wrist. Based on a radiological examination of skeletal development of areas of the non-dominant hand and wrist, the bone age is assessed and compared to the chronological age. A discrepancy between these two values indicates abnormalities in skeletal development. This examination is performed on children with growth abnormalities to affirm clinical suspect, to predict height at adult age, or to monitor the effect of treatment of metabolic diseases.

A common method for assessing the skeletal maturity is the atlas method, and the hand-wrist was the first area of the body for which atlases became available. Currently, there are two frequently used atlas methods operating on a hand-wrist radiograph.

The most frequently used method (78%) is the Greulich and Pyle (GP) method. In this method, the radiograph of non-dominant hand wrist (mostly the left hand) is compared to a reference series of hand-wrist radiographs displayed in this atlas. Each hand-wrist radiograph corresponds to a certain year of bone age. The age interval between successive hand-wrist plates varies from 3 to 6 months. The reference radiograph, which globally compares best with the clinical image, is selected as the best match and its associated age is called the bone age. This atlas-derived bone age is then compared with the chronological age of the patient, and the age difference is used for diagnostic purposes.

The manual effectuation of this method is prone to error or susceptible to ambiguity.

Firstly, different radiologist performing this procedure may have different training experience; hence substantial inter-observer and intra-observer variance may result from the subjective nature of this comparison.

Second, the comparison is a global one. Depending on the weight the radiologist attaches to the similarity or dissimilarity of specific skeletal sites on the hand-wrist radiograph, ambiguous results may be obtained.

A method, which aims at minimizing the subjective observer errors, is the Tanner and White house method (TW2 method). Scores are assigned to grades of skeletal maturity indicators, and the sum of scores is later transformed to a skeletal age (also called bone age). Slight modifications to the reference values and charts have recently been made to reflect changes in the population, resulting in the TW3 method. Descriptions and manual rating of the stages of the bones, however, have not been altered.

The TW2 method is currently effectuated in paediatric radiology as follows.

A radiograph from the non-dominant hand and wrist is made either by (a) conventional screen/film recording system, or (b) by digital means such as film digitisation, a computed radiography system or a direct radiography system (based on direct or indirect flat panel, or CCD).

In case a film is used, it is viewed on a light box. A digital image on the other hand may be either printed on film and viewed conventionally on a light box, or it may be displayed on a viewing station.

Knowledge of gender and chronological age of the patient are the only two clinical data needed to start the analysis.

For each skeletal site indicated in the atlas for which a score needs to be established, the corresponding skeletal site in the actual hand-wrist radiograph is searched for visually. Specific salient anatomic details of the skeletal site are retained mentally.

Then the attention is directed to the different stages depicted in the atlas to identify the most similar one.

Use is made of (1) the reference pictures (two radiographic reproductions per stage in the TW2 atlas, to reflect the range of variation within the stage), (2) a sketch or drawing of the skeletal site depicting the outline of the bones, the radio-opaque lines on or within the margin of the epiphyses and bones and pointers to salient features of the particular stage, and (3) one or more criterions per stage, which are textual explanations hinting at the most prominent image features of the stage.

In the event of doubt, whether a particular feature of a certain stage is present or not in the actual image, visual attention is redirected back to the hand-wrist image on the light box or computer display.

As a matter of course, the correct skeletal site to be assessed needs again be relocated in the hand-wrist radiograph before such confirming visual analysis can be effectuated.

In many cases, if not all, several switches back and forth between hand-wrist radiograph and the reference stages in the atlas are needed before a conclusive assignment of a reference stage can be made.

The score, corresponding to the matching stage, is written down on paper or typed in a computer spreadsheet or database.

This iterative process of hypothesis generation and hypothesis verification as to the actual stage of a skeletal site is repeated s for every skeletal site.

In the full TW2 method, 20 skeletal sites in the hand-wrist need to be assessed this way; therefore this scoring method can be time-consuming, demanding and error-prone.

The total score (on a scale between 0 . . . 1000) is translated into a bone age by a table look up operation. A different table is applied depending on the gender of the patient.

The bone age derived is compared with the chronological age of the patient and the difference between them is used as an element in the clinical diagnosis process.

Analogous to the Greulich and Pyle method, care must be exercised when interpreting the bone age to chronological age difference for patients belonging to a race other than the Caucasian type, because the atlas shows reference pictures and associated scores for this ethnic type only.

Unfortunately, although reliable, the above method is complex to operate for several reasons:

It requires a well-trained radiologist or radiology operator.

Because it requires the assessment of a great number of different skeletal sites, a manual method is time consuming.

The application of the method by means of analogue screen-film radiography is particularly cumbersome. It requires 3 distinct media to effectuate this procedure:

An X-ray film of the hand or other skeletal sites, displayed on a light box. With the emergence of digital radiography modalities (film digitisation, computed radiography, digital radiography sensors), the digital image may be displayed on a computer display instead. However, such electronic medium still is physically distinct from the remaining components.

The TW2 atlas illustrating the different reference skeletal stages to compare with, and depicting the conversion table to manually convert the total score into a bone age.

Pencil/Paper to note and add the scores of each selected stage in the patient dossier. Alternatively, electronic spreadsheets may be used in conjunction with a database to store and compute the total score and the conversion to bone age. This way of operation is particularly cumbersome when scores determined at regular time intervals need to be retrieved and compared for clinical evaluation over time.

Both TW2 and GP atlases have been established for the Caucasian racial type. Therefore, the bone age derived from these atlases is in principle valid for this type only.

Another example of an application wherein radiographic scoring is used, is rheumatoid arthritis.

Conventional rheumatoid arthritis scoring (RA scoring) is based on comparison of the actual film radiography of hands and feet with reference pictures printed on film.

To establish the database of reference pictures, all stages of a joint or a group of joints are printed on one sheet of film in life size.

Scoring proceeds by displaying standard reference films and the actual radiography on a light box, and writing down scores associated with the matching stage of each joint.

Among other indicators, the most specific deformations in RA are erosions and joint space narrowing. The radiological study of these deformations is complementary; therefore, both are being assessed in a scoring method.

Radiological assessment serves as a recognized standard for the evaluation of rheumatoid arthritis. For standardized, epidemiological and therapeutic evaluation, scoring or grading systems have been proposed on X-ray images of specific skeletal sites. X-ray images have the advantages to be able to record the history of the damage of a joint, because the damage is mostly irreversible. Previous images can be recalled in a later stage, to assess the evolution and to subject them to newly developed scoring systems. The effectivity of drugs can be traced.

These advantages however, can only be obtained when the images are of sufficient diagnostic quality: (a) for serial assessment, the positioning of the joints during radiation exposure are of substantial importance, (b) correct exposure is important because overexposure or underexposure affects e.g. the correct assessment of erosions, and (c) the images recorded with sufficient resolution are essential for a reliable evaluation of previous erosions.

Still another example of an application wherein radiographic scoring is used, is osteoporosis scoring.

Spine or hip fracture due to minor or no trauma is an essential feature of symptomatic osteoporosis. Conventional radiographs are widely used to confirm or disprove suspected osteoporotic fractures, and may also demonstrate progress of existing fractures or development of new ones.

The scoring systems using conventional radiographs suffer the same drawback of other film-based diagnostic scoring systems. As indicated, the problem of repeated re-location of the anatomical site is even more compound because the spine is a highly repetitive structure of vertebrae having almost identical shape.

OBJECTS OF THE INVENTION

It is an object of the present invention to provide a user-friendly radiographic scoring method that overcomes the drawbacks of the prior art scoring methods, such as the need for different media and the need for repeated focusing of the attention between images on different media.

Further objects will become apparent from the detailed description given hereinafter.

SUMMARY OF THE INVENTION

The above-mentioned objects are realised by a method of radiographic scoring of a radiographic image comprising the steps of acquiring (1) a digital image representation of an image to be subjected to radiographic scoring, applying (2) the acquired image representation to a display device and generating a displayed image, determining (3) at least one region of interest on the displayed image, retrieving (4) for each of the determined regions of interest a number of reference stage images from a database (5), each reference stage image having an associated score number and displaying (6) the reference stage images on said display device, selecting (7) a displayed reference stage image which most optimally matches with a displayed region of interest, associating (8) a score number corresponding with the selected reference stage image with the displayed region of interest, combining (9) score numbers associated with said regions of interest into an overall score number pertaining to said radiographic image.

A displayed reference stage image which most optimally matches with a displayed region of interest can be selected by displaying each of said region(s) of interest and the reference stage images pertaining to the displayed region of interest in close proximity to each other, and visually comparing a displayed region of interest and displayed reference stage images pertaining to the displayed region of interest, selecting a displayed reference image which visually most optimally matches with a displayed region of interest.

A reference stage image is an image which is representative for a developmental stage of a specific skeletal site. These reference stage images are commonly selected by an expert. In most cases these reference images are accepted as world wide standards.

In one embodiment the step of determining a region of interest is guided by means of a stencil consisting of a sketch of a body part of the patient that is to be evaluated. The sketch depicts at least one of the outline of the following three items: the body part, bone contours of bones within the body part, anatomical contours, as well as region of interest delineations superimposed on said sketch.

In one embodiment a region of interest is determined and extracted on a display device by manual operation.

The following steps are performed:

displaying a stencil comprising a sketch of a body part to be evaluated and region of interest delineations superimposed on said sketch, mapping or dragging the region of interest delineations onto the actual position of the body part to be scored in the displayed image, adjusting the shape of the region of interest by rotation and scaling so that it substantially matches the actual geometry of the local anatomy in the displayed image, selecting image data within the dragged delineations as region of interest.

In one embodiment a digital image representation of a region of interest is extracted from a digital image representation of said image by re-sampling and interpolation.

Preferably a stencil is selected according to identification data of said radiographic image such as gender, age and examination type (hand, foot etc.).

After the regions of interest superimposed on the skeletal outlines in the stencil, are mapped to the correct position in the image, the image data in the regions of interest in the displayed image are extracted. Preferably the extracted regions of interest are subjected to rotation or to an affine transformation so as to have them in upright position.

Regions of interest may also be subjected to image enhancing processing (see below).

Next the ensemble of ROI's is subjected to the remainder of the scoring steps: display in proximity to the reference stage images, selection of the best matching reference stage image, associating of a score number and combining of score numbers of all regions of interest into an overall score number of the entire image.

This procedure is referred to as manual scoring procedure.

Alternatively a semi-automated method can be applied wherein all steps of the method described higher are also applied but wherein additional decision support is generated to assist the selection of the optimally matching reference stage image. In this semi-automated method additional support is generated to help to assess whether a specific feature is radiologically manifested in the region of interest. More specifically for each of the regions of interest (ROI) a sequence of specific image processing operators is applied to compute ROI specific feature values and to subject the computed feature values to a judgment device in order to determine presence or absence of a feature. Presence or absence of a feature will be used for assessing which reference stage image is most optimally matching. This system is called semi-automated scoring since the ultimate decision whether or not a computer-suggested decision is accepted, is still made by a radiologist. It may be possible in the current method that not for all regions of interest automatic feature based support is available. Furthermore it may also be possible that the features are not computed exhaustively for all stages of a specific region of interest.

In an enhanced semi-automatic operation mode all features applicable for a specific region of interest are computed and input to a judgment device to derive the stage of the region of interest. The difference with the above semi-automated method is that, in order to derive a suggestion as to the stage of the region of interest, all relevant features covering the whole developmental stage of the spectrum of the region of interest must be computed and used in the classification process. The only task left for the radiologist is then to accept or reject the computer suggestions for individual features. This form of semi-automated scoring will therefore be much faster, but because of the plurality of input features, the judgment device is faced with a more complex task. Bayesian classifiers and artificial neural networks are used for this purpose.

Data within a region of interest and/or data of a reference stage image may be subjected to image processing. Image processing is e.g. spatial reformatting and/or processing for the purpose of enhancing the intrinsic image quality. For example multi scale contrast enhancement can be applied, as will be explained further on.

Another aspect of this invention relates to a computer program product as set out in the claims.

Further details of the different steps performed by the computer program product are set out in the dependent claims.

A computer program product is meant to encompass a software product in the form of an electric signal as well as a computer program on a computer readable medium such as a CD-ROM.

Still another aspect relates to a computer readable medium such as a CD-ROM comprising program code adapted to carry out the above method.

Specific features for preferred embodiments of the invention are set out in the dependent claims.

It will be clear that the scoring method according to the present invention copes with the problems of the prior art.

The ROI extraction and display in the neighborhood of the reference stage images alleviates the problem of repeated focus of attention towards the correct skeletal site.

Furthermore, by applying image processing such as multi-scale enhancement, the available dynamic range of the output medium can be used optimally to render all relevant image details.

The current invention is particularly suited to implement different variations of the Sharp score in rheumatoid arthritis, since the ROI stencil can be customized so as to include only an abbreviated set of ROI's.

Alternatively, a score, based on a reduced number of ROI's, can also be derived from a superset including more ROI's having been evaluated previously.

The risk to evaluate a wrong ROI is substantially reduced, because the ROI stencil depicting fewer skeletal sites serves as a reliable hinting mechanism.

In the prior art the task of focusing on a ROI and scoring is alternated for all skeletal sites. In one embodiment of the present invention the order has been changed, first all ROI's are determined and next the scoring is performed.

In the field of osteoporosis the invention is particularly useful since by first extracting regions of interest around each vertebra, the visual search process is greatly simplified. No confusion with other vertebrae is possible when presenting each ROI in juxtaposition with the reference radiographs and graphic pictures.

For bone age determination, errors that might occur in the prior art due to inadvertently exchanging score numbers for boys and girls, are avoided.

BRIEF DESCRIPTION OF THE DRAWINGS

FIG. 3 is an example of automatically segmented RUS bones, wherein FIG. 6 is an example of a user interface with static ROI display.

DETAILED DESCRIPTION OF THE INVENTION

Image Acquisition and Display

Figure 1:
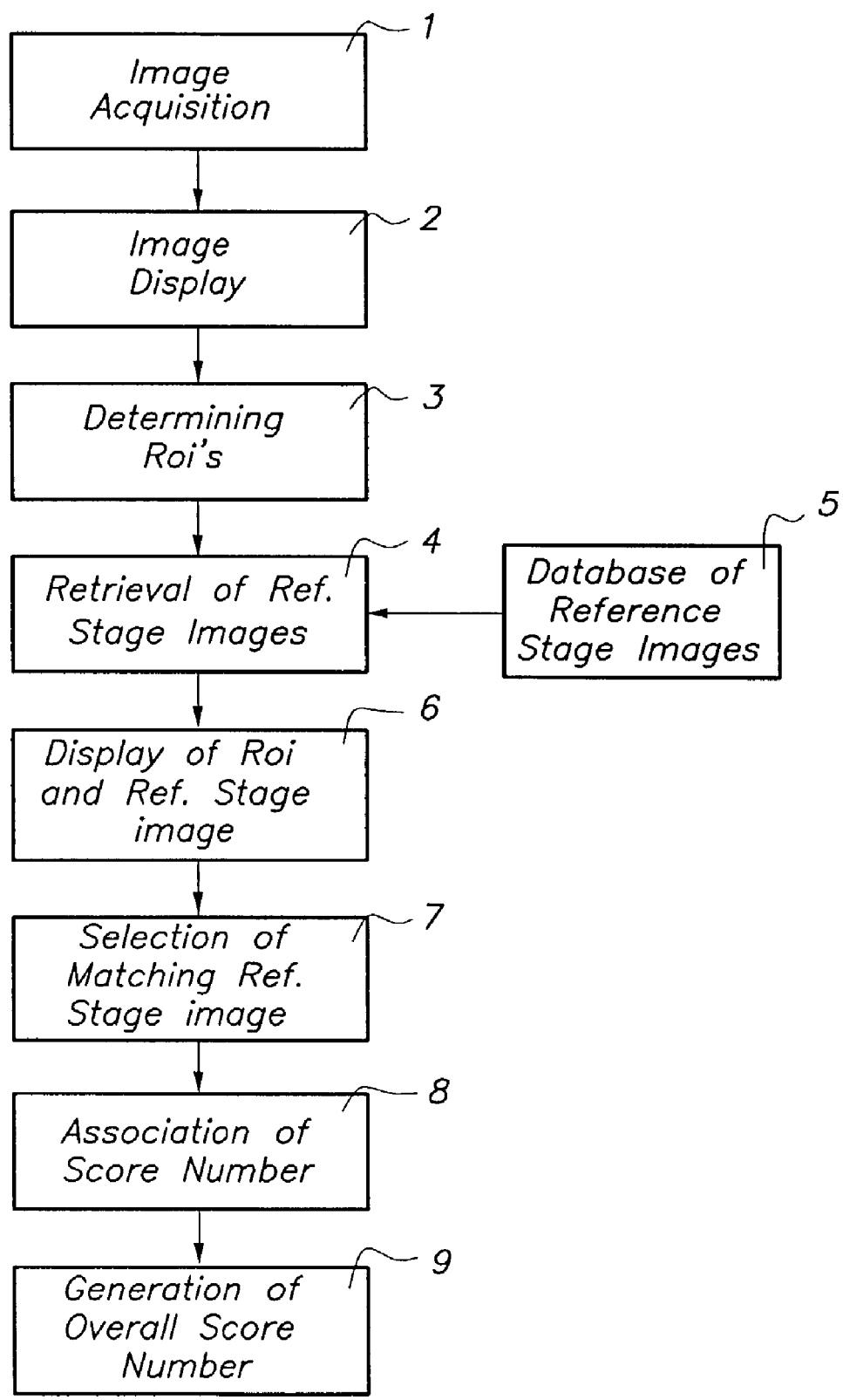
FIG. 1 illustrates the different steps of a scoring method according to the present invention.

A digital image representation of an image to be subjected to radiographic scoring is acquired (FIG. 1, numeral 1).

A large variety of image acquisition systems are applicable. The radiation image can for example be recorded on a photostimulable phosphor screen. The screen carrying the radiation image is then read out by scanning it with stimulating radiation and detecting the image-modulated light which is emitted upon stimulation and by converting the image-wise modulated light into a signal representation of the radiation image.

In an alternative embodiment the radiation image can be stored in a direct radiation sensor rendering a signal representation of a radiation image.

Still further alternatives for acquiring a digital signal representation of a radiation image, such as scanning of radiographic film carrying a radiation image, are possible.

The acquired image representation is next applied to a display device and the image is displayed (FIG. 1, numeral 1).

ROI Positioning and Selection

Next, in the ROI (region of interest) positioning stage at least one ROI is determined on the displayed image (FIG. 1, step 2).

In the following explanation will be referred to the hand as a body part that is subjected to evaluation. However, the present invention is not limited to scoring methods using the hand as a body part to be evaluated.

In this context, the region of interest is the image region covering the joint or bone relevant for the examination. The ROI positioning stage aims at positioning all regions of interest (ROI's) on the body part that is examined. Although each of the ROI's may be extracted separately and analyzed immediately, a more convenient work flow is obtained by first extracting all ROI's simultaneously before processing them.

ROI positioning can be performed in an operator-guided way or alternatively in an automatic way.

In the case of operator-guided ROI positioning a method using a digital stencil can be used to facilitate the positioning.

In this context, a stencil is a digital sketch of a hand wrist image depicting the outline of the hand and all hand bone contours. The delineations of all possible ROI's are superimposed on these outlines.

As has already been explained higher, a hand-wrist image is taken as an example. Other body parts may be examined depending on the type of application and the radiographic scoring method.

For example for the TW2 analysis, these ROI outlines will typically be rectangular regions around joints of the tubular (radius, ulna, metacarpal and phalange) bones and around the carpal bones.

Figure 2:
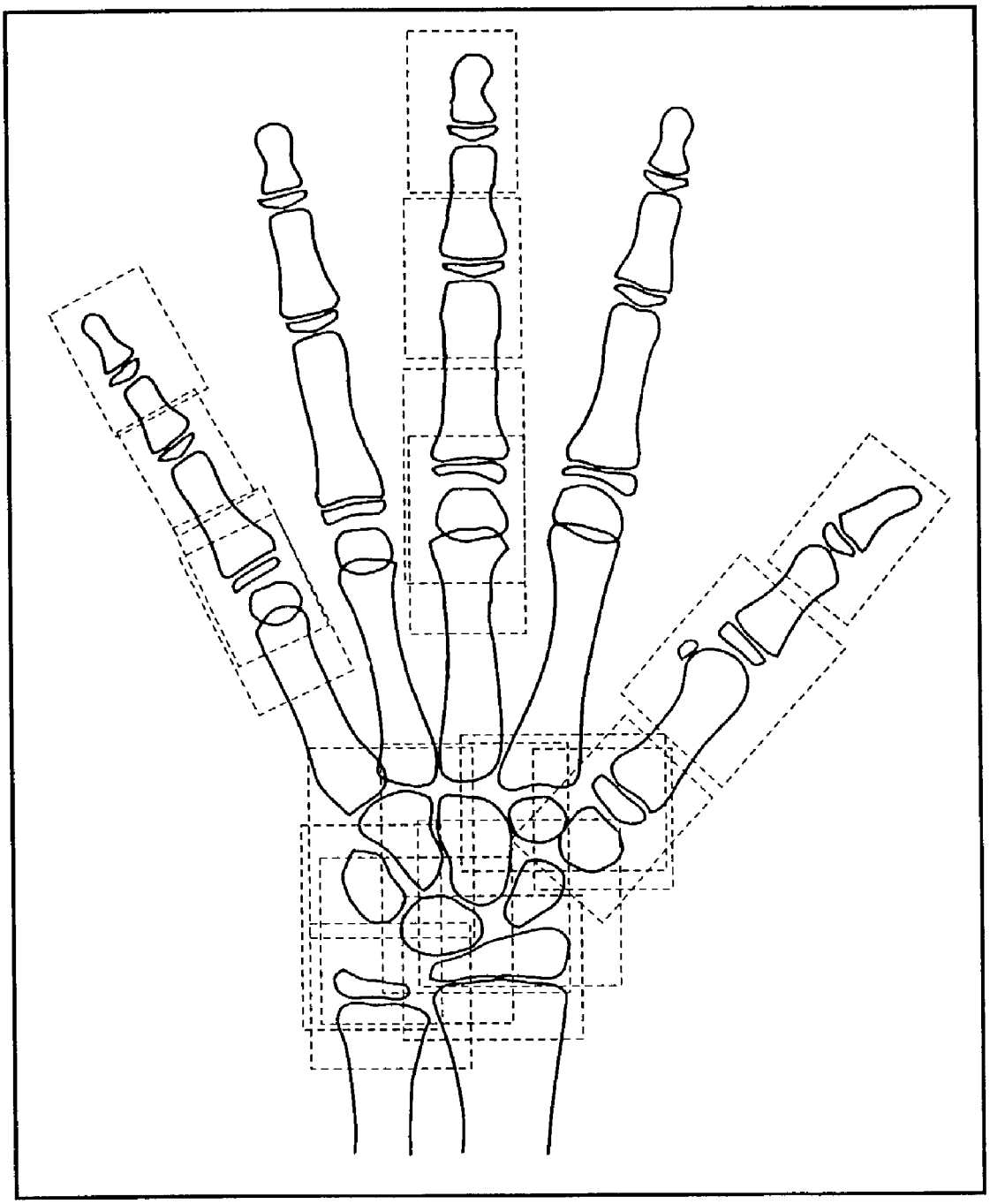
FIG. 2 shows a stencil used for bone age determination.

FIG. 2 shows a stencil used for bone age determination. The stencil shows all rectangles of regions of interest (dashed lines) superimposed on an outline of the diagnostic entities.

Each of the ROI outlines is mapped or dragged by the operator (translated e.g. by mouse and arrow keys) to its actual location in the displayed image, and the stencil serves as a guideline to indicate the intended image region the ROI should encompass, with sufficient precision for further analysis.

Basic operations such as translation, rotation and scaling may be applied to the stencil ROI so that the resulting ROI fully comprises its associated hand bone without irrelevant bones being present which would make the identification of the target bone ambiguous.

The manual placement may be speeded up by first translating, rotating and scaling the stencil in its entirety so that it roughly coincides with the actual hand and bony outlines, and by further adjusting the position of the individual ROI's so that each ROI accurately covers its intended bone/joint location.

An alternative for speeding up is the semi-automated positioning relative to a few user-defined points.

Because the superposition of all ROI's in the stencil may be visually confusing when they overlap substantially (this is especially the case for the carpal region of interest), the ROI's may be sequentially displayed in the stencil and positioned in the actual region. Size and orientation of the rectangles may be modified e.g. by corner point dragging to match the actual size and the orientation of the displayed image.

Because the hand-wrist anatomy changes its aspect in accordance with age, the stencil must preferably reflect this in order to more faithfully represent the actual skeletal sites. Therefore, preferably a number of hand-wrist stencils are stored as a function of chronological age, gender, race etc. In accordance with the patient's identification data such as age, race, gender, etc. which may be entered into the computer, the corresponding sketch can be selected.

Although the chronological age may not be representative for the skeletal maturity status of the patient (the bone age scoring is precisely meant to detect significant differences from it), it serves as a rough estimate for the initial selection of the stencil.

In an alternative embodiment, the ROI positioning can be automated by image processing algorithms, so that no user interaction is required in the placement of the ROI regions.

Automatic placement can be based on first automatically segmenting the bones based on Point Distribution Models (PDM) and Active Shape Models (ASM) such as disclosed in the prior art (Cootes TF and Taylor CJ, Active Shape Models—"smart snakes", Proc. British Machine Vision Conference, Springer Verlag 1992, p. 256–275). An example for segmenting the individual vertebrae in the spine is given in (Smyth et al, Automatic measurement of vertebral shape using active shape models, Image and Vision Computing, Vol. 15, p. 575–581, 1997), for the hand and hip in (Behiels et al, Active shape model based segmentation of digital X-ray images, proceedings 2and international conference on medical image computing and computer-assisted intervention—MICCAI'99, lecture notes in computer science, Vol. 1979, p. 128–137, 1999).

Secondly, depending on the scoring method, the ROI's searched for may be located in the following ways with respect to the segmentation of the bones:

at outer borders of the bony segmented regions (which is the case for RUS bone age scoring because the proximal and distal interface regions of neighboring bones contain the epiphyses and corresponding metaphyses; and for rheumatoid arthritis scoring, because these regions are affected by joint space narrowing and is erosion defects), around the bony region (which is the case for individual vertebra of a spine, such that each ROI contains the segmented vertebra and part of both neighboring vertebrae), inside the bony region at pre-determined locations given by human anatomy (which is the case for carpal bone age scoring when the region of carpal bones is segmented as a whole, because the each carpal bone has a fixed position with respect to all other carpal bones contained in the ROI).

Figure 3A:
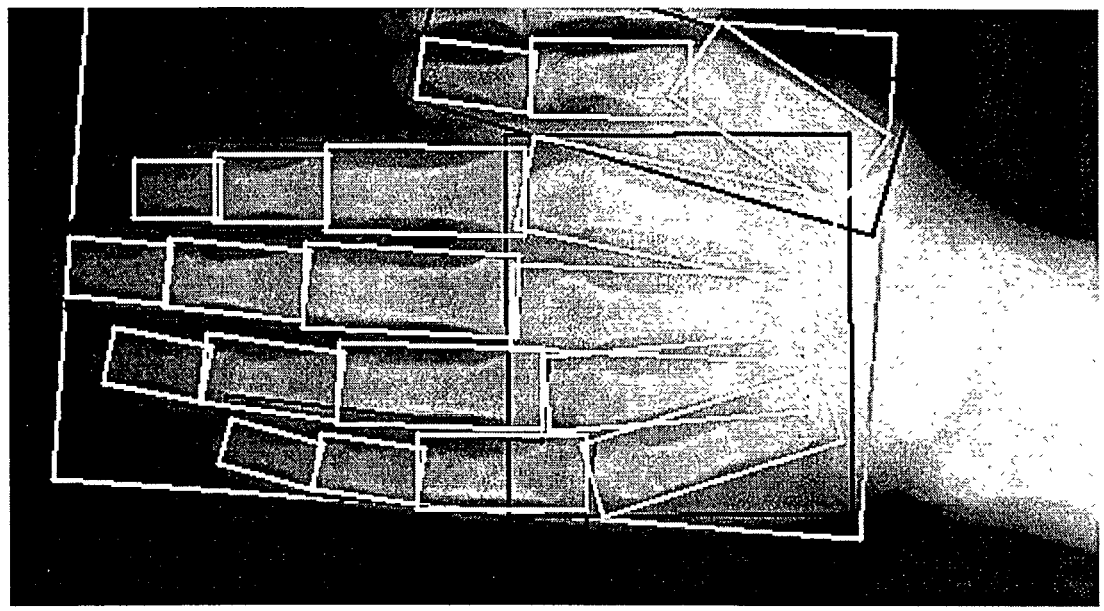
FIG. 3A shows the initial bounding box placement for automatic segmentation of the associated bones and FIG. 3B shows the segmentation of the phalanxes and carpal bones. The interface regions at the extremal ends of these bones determine the ROI's for bone age scoring.
Figure 3B:
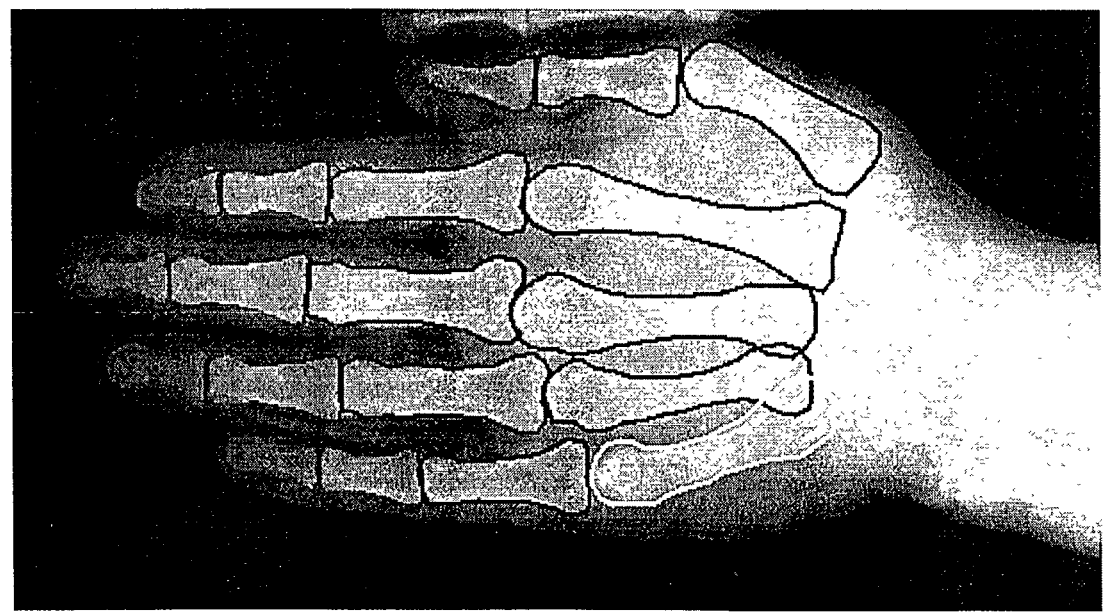

FIG. 3 is an example of automatically segmented RUS bones. FIG. 3A shows the initial bounding box placement for automatic segmentation of the associated bones and FIG. 3B shows the segmentation of the phalanxes and carpal bones. The interface regions at the extremal ends of these bones determine the ROI's for bone age scoring.

Scoring Procedure—General Overview

The methodology used to achieve radiographic scoring according to the present invention will be described using bone age assessment as an example.

Whenever necessary, details specific for other clinical scoring methods( rheumatoid arthritis, osteo-arthritis, osteoporosis and ankylosing spondylitis) will be indicated.

Figure 5:
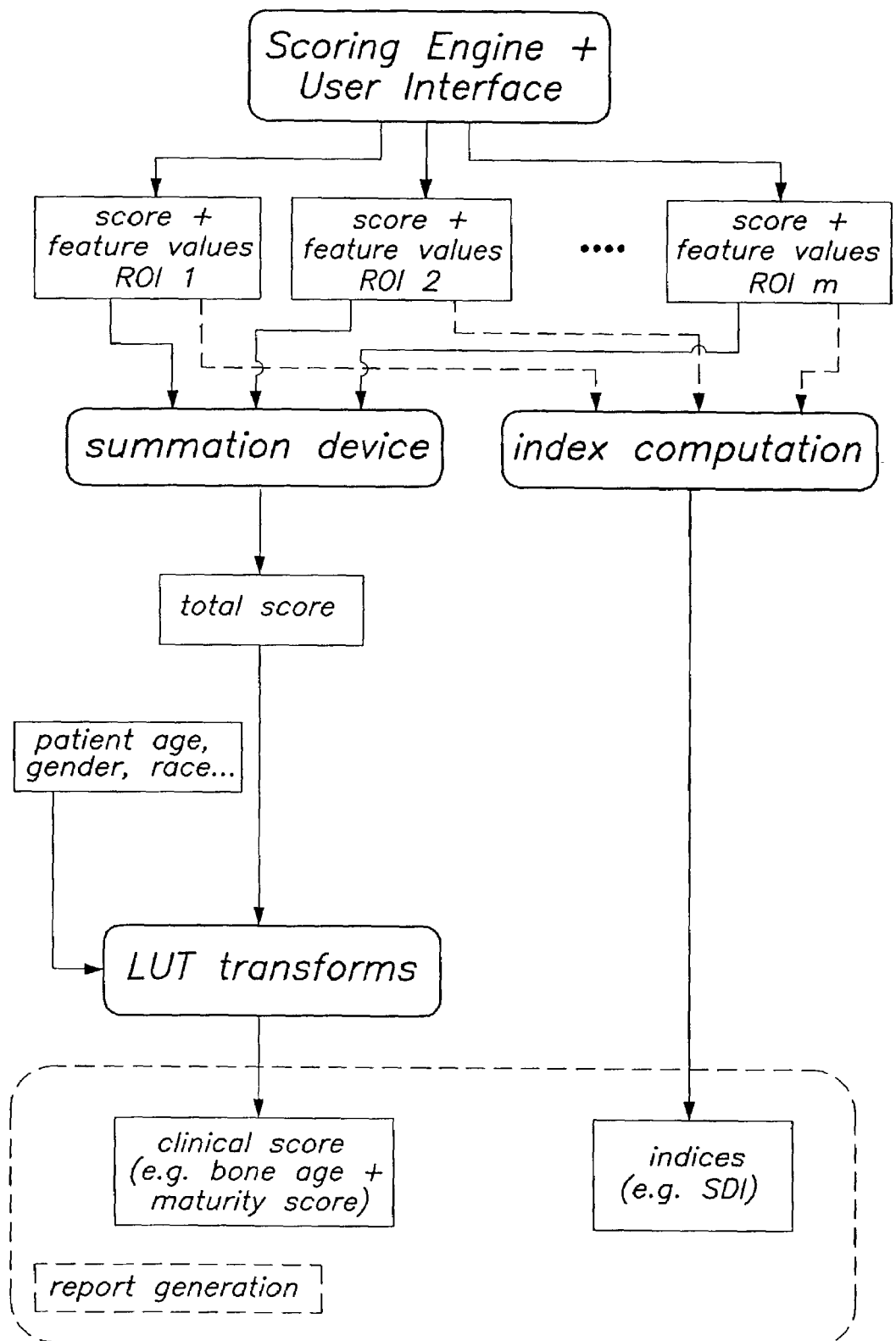
FIG. 5 is a general overview of a scoring system.

A general overview of a scoring system is shown in FIG. 5.

The system comprises an engine and a user interface. The engine controls the navigation through different screens (e.g. one screen per region of interest), retrieves and supplies the previous scores and regions of interest from the database, controls juxtaposing of the regions of interest and the reference stage images on the display device, initiates appropriate image processing of the region of interest (e.g. contrast enhancement) and geometric manipulation (e.g. zooming) to optimize visual matching, initiates computation of ROI features on the radiologist's request for decision support, updates spreadsheet and database for newly retained region of interest scores.

The summation device requires the individual score values of the regions of interest (and feature values) as input values and computes and outputs a total overall score of the radiation image.

It may further compute sums of features which are output as an index (as will be explained further on).

The total score output by the summation device may be subjected to LUT (look up table) based transforms (the exact transform being dependent on the patient identification data) to convert the overall score to a clinical score value.

A report may finally be generated.

Comparison of ROI's with Reference Stages

Referring again to FIG. 1 (numeral 4), in the following step a radiologist or radiology operator visually compares each ROI with reference stages so as to find the most optimal matching stage. This procedure is performed successively for every ROI.

To this end a data base (FIG. 1, numeral 5) is composed in advance. The database comprises for each individual ROI a number of reference stage images corresponding with different developmental stages, each of these reference images having an associated score.

Figure 7:
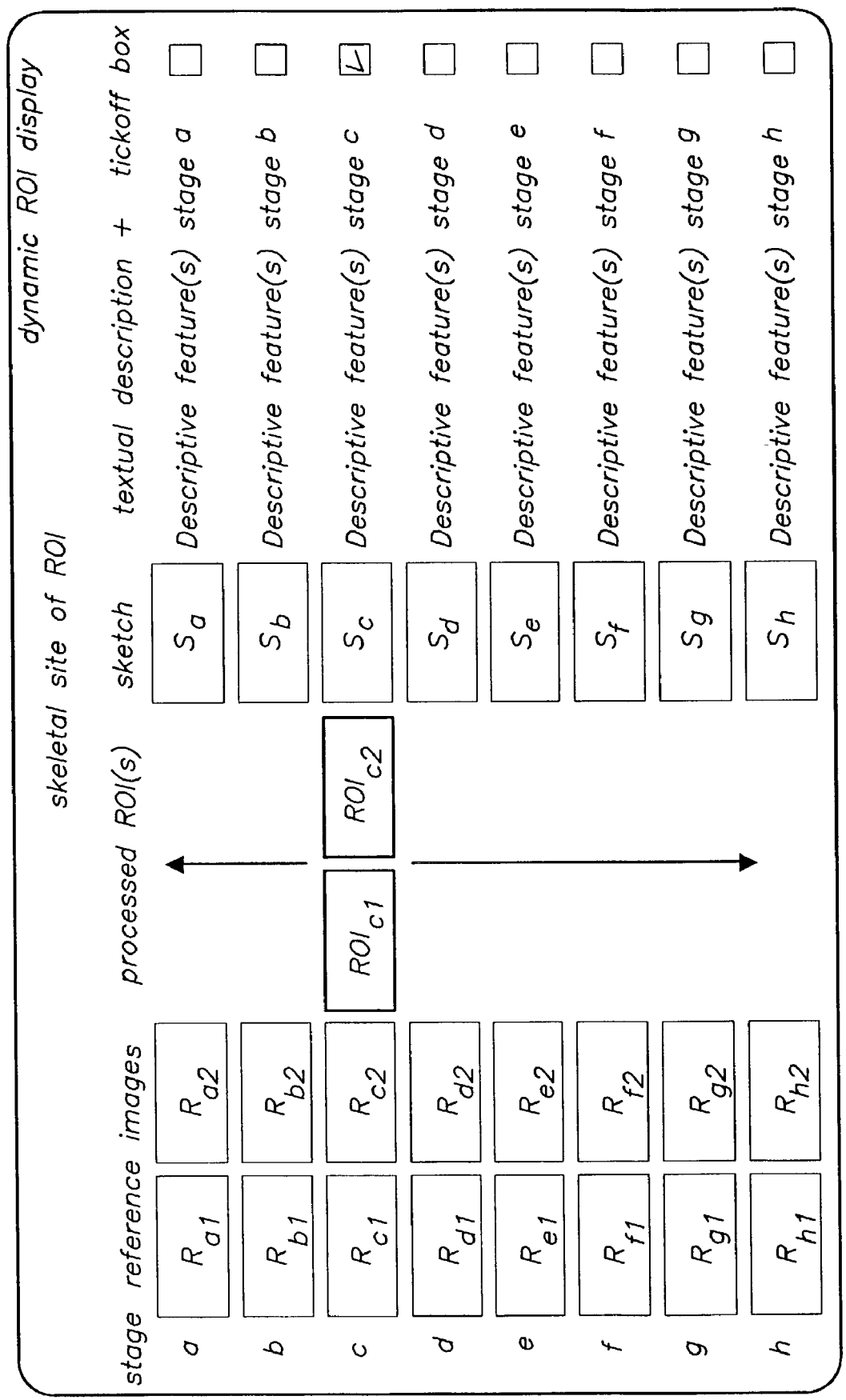
FIG. 7 is an example of a user interface with dynamic ROI display.

To facilitate this comparison, a graphical user interface has been developed. FIGS. 6 and 7 show different embodiments of the organization of a graphical user interface on a computer screen used for performing the scoring procedure on each ROI.

In the user interface a number of reference images having an associated score number are displayed for each of a number of stages.

In one embodiment all reference images according to a certain stage are displayed on the same row (referred to as the row-wise arrangement). Reference images corresponding with different stages are displayed in different rows. If the number of stages (hence the number of rows) exceeds the display capacity of the screen, a scroll able window can be used. In the illustrated embodiment the leftmost two columns depict a set of reference images, two images per stage. Up to 8 stages (stage B to I) are used in the bone age assessment.

This embodiment of a user interface according to the present invention further comprises means for displaying one or more regions of interest ROI of an image to be scored. The display of the region of interest is situated in close proximity to the display of the reference image(s). In the displayed embodiment the third column is reserved for the display of the actual ROI to be classified.

In the illustrated embodiment a fourth column is provided which depicts a sketch of the bone with emphasis of particular anatomic features.

A fifth column may also be provided which displays a list of salient anatomical feature(s) in textual format, one or more for each of the different stages.

Means may be provided for displaying a tick close to the textual information for ticking off the textual information so as to indicate the fact that the radiologist perceives the feature in the actual ROI of the skeletal region.

It will be clear that the columns may be interchanged without substantially changing the classification process. For example, the actual ROI image may be placed in between the two reference images, instead of being placed between the reference image and the sketch image. Also, more than two reference images per stage may be used to achieve broader coverage of the grey value appearance of a certain stage.

Instead of a vertical arrangement of the reference data, a horizontal arrangement may be adopted, and the actual ROI may be slided horizontally through the scoring screen. Because all reference elements of a certain stage are positioned in the same column, this disposition is called the column-wise arrangement.

Two modes are available for displaying the ROI's in the scoring screen.

A first mode is the static mode in which each ROI is displayed in juxtaposition with all reference stage images.

A second mode is the dynamic mode in which a single ROI is displayed juxtaposed to reference stage images. This ROI is shifted up and downwards by user interaction e.g. by mouse movement, and is juxtaposed to the next or previous reference stage images.

Selection of Matching Reference Stage

The reference stage which most optimally matches with the displayed ROI is selected (FIG. 1, numeral 7) and the score number associated with the selected reference stage is retained (numeral 8) for generating the total score number of the total image (numeral 9). The total score can be generated as the sum of the individual scores of the ROI's. Additionally an index can be calculated, being a more complex accumulation of feature values pertaining to individual ROI's (e.g. SDI—spinal deformity index).

The interactive comparison of only (a) region(s) of interest of the hand-wrist X-ray image has major advantages over the comparison of the entire hand-wrist X-ray image with a reference image.

Because the actual region of interest only comprises the skeletal site to be classified without any extraneous anatomical detail visual comparison and stage assignment is made easier than in prior art methods. Also because in the present user interface a region of interest can be juxtaposed to the reference images and the sketch, the visual comparison and stage assignment is greatly facilitated over the prior art method.

Maturity Indicator

A radiographic feature of a skeletal site that assists in the assessment of the skeletal maturity is called a maturity indicator. A maturity indicator must be determined during the maturation of every child to be useful in the assessment of maturity. By definition, the grades of a maturity indicator appear in a fixed sequence for each bone, irrespective of stature, weight, health or other socio-economic factors.

This characteristic of human growth can be exploited in the user interface according to the present invention in the following way.

Stages and corresponding scores can be recalled from the archived data and displayed during assessment of the maturity of the current skeletal site. In the assumption that the scores previously assigned to a specific skeletal site are correct, the score to be assigned to a ROI of this site under current evaluation cannot be less than the previously assigned score.

Likewise in rheumatoid arthritis previous damage to the skeletal site cannot be undone. The score number of the last evaluation is carried forward to the present evaluation.

This property can be implemented in a specific embodiment of the user interface according to the present invention by disabling all reference stages that are less mature or that correspond to a less deteriorated stage, thus narrowing the search in a plausible manner. Such stages can be disabled e.g. by graying them out.

Still further narrowing the set of assignable stages can be achieved by marking, e.g. ticking off a characteristic feature in the textual information section on the scoring screen of the user interface. The user interface is then organized such that whenever such a feature of a certain stage is deemed to be present, no less mature stages can be selected. Reversely, when a feature of a certain stage is believed not to be present, said stage and all more mature stages are put to a non-selectable state.

Furthermore, to clarify the decision support, the time sequence of the archived regions of interests for a particular skeletal site can be displayed along with the chronological time at which each radiograph has been taken, so that the evolution over time can be assessed.

The duration of each maturity indicator can be determined and displayed graphically, thus showing how long the bone remained at the same level of maturity.

Figure 8:
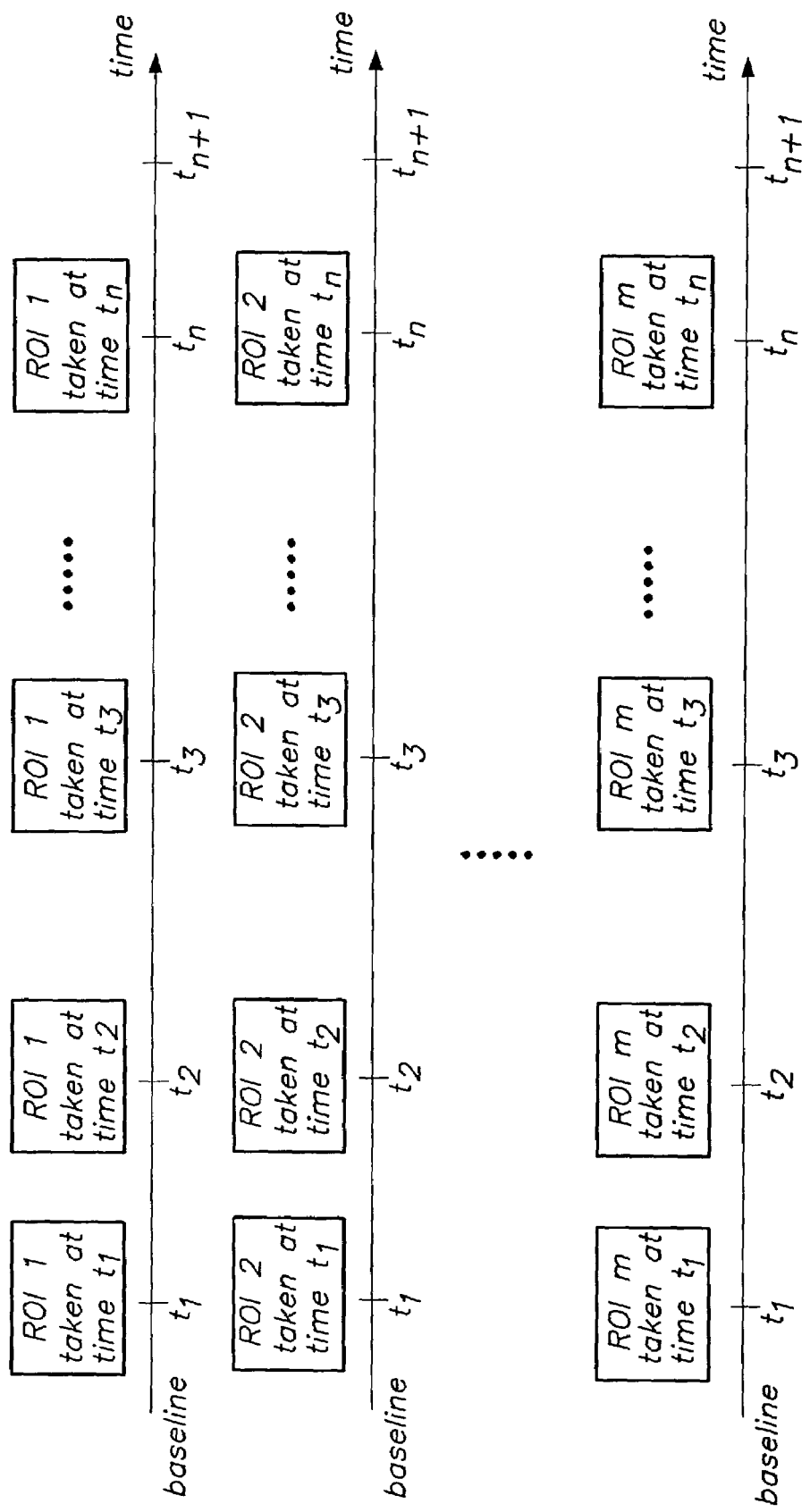
FIG. 8 is an example of a longitudinal maturity study.

In order not to miss stages, schedules of serial (follow-up) radiographs can be planned relative to the inception of maturity indicators as opposed to classical chronological age planning. This feature is termed the longitudinal maturity study and the screen layout is depicted in FIG. 8. Time $t_1$ is called baseline and is the point in time at which the first scoring was made. Distances along the time axis are proportional to the time of actual exposure of the radiographs. Time $t_{n+1}$ is a time point in future at which a new scoring is planned, depending on indications derived from the visual analysis of the ROI sequences. The screen is made scroll able to allow for a large number m of ROI's or a large number of scoring studies over time.

While the statement, that the sequence of maturity indicators is always the same, is true for the grades of a single indicator for a particular bone, it is not accurate if-applied to several indicators of various bones. Precisely because each skeletal site is assessed separately, this characteristic of local differences in human bone growth does not influence the precision of the TW2 method, in contrast to the global method of Greulich and Pyle where all skeletal sites must be assessed simultaneously.

The availability of the reference data in digital format enables more easily customisation towards the ethnic type. Currently, the TW2 atlas has been established for the Caucasian type. Differentiation towards ethnic type is achieved either by supplying reference pictures and associated scores according to the patient's ethnic type, or by substituting new value of the TW2 scores only and keeping the classical reference pictures. This type of customisation obviates the need for establishing different atlases in the current operation of the TW2 method.

A TW3 atlas has recently been introduced. The operational principle is identical. The calculation of the total score number has been changed relative to the TW2 atlas in order to match better with the characteristics of the present population.

In the prior art, the scores needed be written down in the patient dossier or added manually into the appropriate database record. In one embodiment of the present invention no recording of the score is needed because the score can be automatically entered according to the row position of the ROI on the screen. On exit of the screen and continuation to the next screen of the next skeletal site, the score can be entered in the spreadsheet and database, running in a background process. The assessor may navigate through the screens to review previously accorded stages, and on leave of the program, an overview of all assigned scores, total score and corresponding skeletal age can be displayed. Graphs, depicting the progression of skeletal maturity of each skeletal site, and overall bone age progression with respect to chronological age, complement the skeletal maturity report.

The embodiments of the scoring methods according to the present invention may have other features distinguishing them from the conventional film-based operation.

Each of the stages of the scoring methods is examined as to their prominent image features. The appearance of these features may be enhanced in a feature-specific way.

Figure 4:
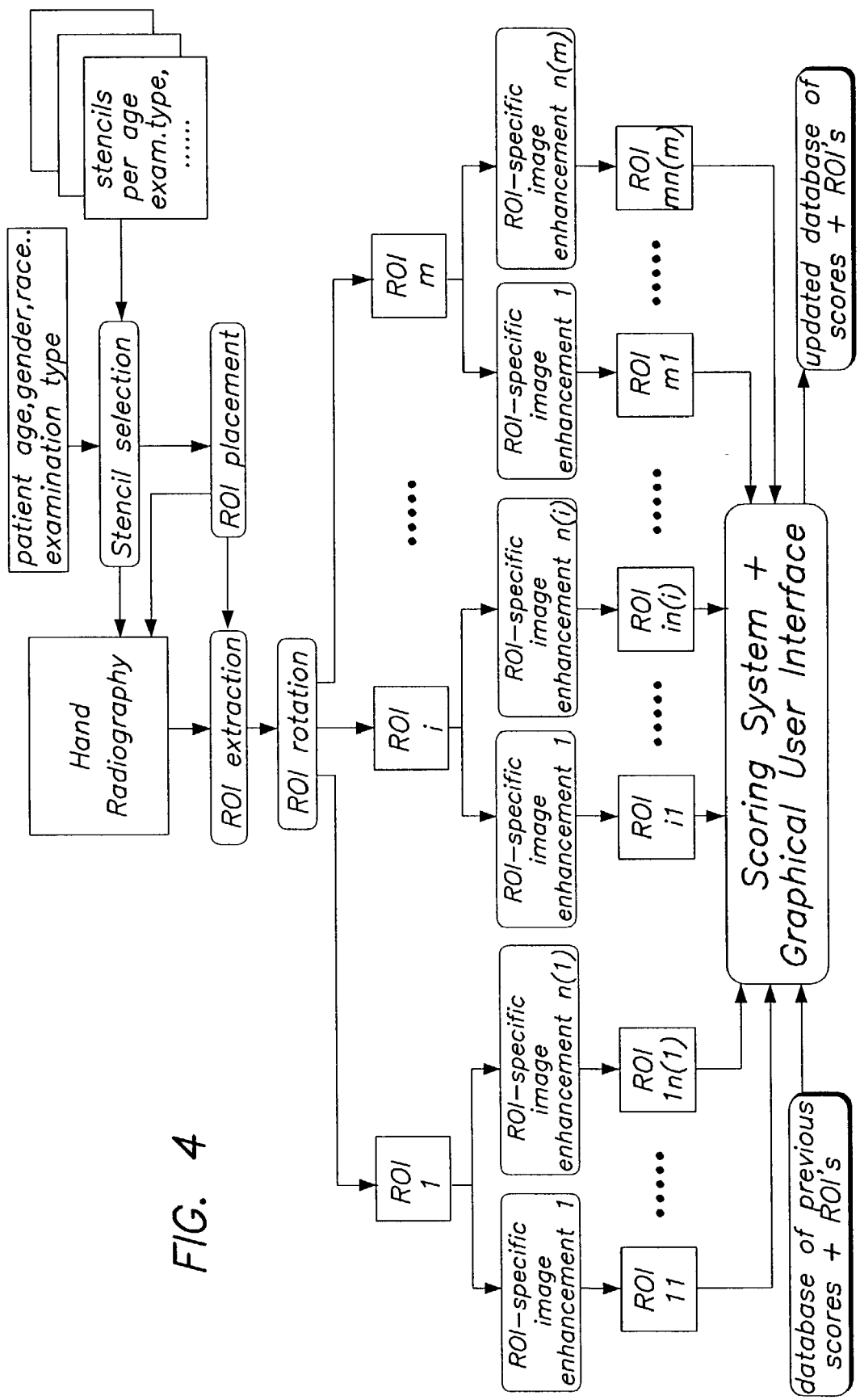
FIG. 4 is a more detailed illustration of a specific embodiment of the method of the present invention.

The application of ROI specific image processing is shown in FIG. 4 which figure gives a more detailed overview of a specific embodiment of the present invention.

In U.S. Pat. No. 5,805,721 image enhancement based on multi-scale image decomposition is disclosed.

An image is decomposed into detail images at different resolution levels and a residual image. The detail images are then modified by applying at least one non linear conversion according to a conversion function which is non-linear, monotonically increasing, odd, and has a slope that gradually decreases with increasing argument values. Next modified detail images and the residual images are recombined to yield a reconstructed, processed image.

Using a suitable transformation of Laplacian pyramid coefficients, different visual aspects of the regions of interest can be enhanced.

Latitude reduction can e.g. be applied for enhanced soft-tissue swelling visualization (RA Larsen scoring) or for enhanced visualization of the onset of ossification (bone age scoring).

Edge enhancement can e.g. be applied prior to width measurement between edges (RA scoring and osteoartritis scoring) or to make assessment more reliable as to whether a border is convex or concave (bone age scoring).

Multi scale contrast enhancement can e.g. be applied to assess the presence of erosions (RA scoring) or to make assessment more reliable as to whether an epiphyses caps the metaphysics (bone age scoring).

If there are more criteria per stage, all applicable processing of the ROI can be performed and displayed simultaneously. Let m be the total number of ROI's, and i denoting the sequence number of a ROI, then a ROI-specific number n(i) of multi scale processing can be performed as depicted in FIG. 4.

These optimally processing of the ROI's are input to the scoring system.

Two modes of displaying the processed ROI's in the scoring screen can be made available:

Static display mode (FIG. 6): all different processing of a ROI are displayed simultaneously in juxtaposition with the reference pictures. User interaction is minimal in this mode (no cursor movements). Selection of the matching stage is achieved by clicking on a row entity (either the most similar reference picture or the particular processed ROI). In this figure $ROI_{a1}$ refers to a region of interest processed to enhance feature 1 of stage a, $ROI_{a2}$ refers to a region of interest processed to enhance feature 2 of stage a etc.

Dynamic display mode (FIG. 7): the displayed processing of a ROI is changed in accordance to the cursor up and down movements. The attributed stage corresponds to the row position of the ROI on leave of the screen. In this figure $ROI_{c1}$ refers to a region of interest processed to enhance feature 1 of stage c, $ROI_{c2}$ refers to a region of interest processed to enhance feature 2 of stage c.

The user may navigate back and forth through the screens corresponding to the different skeletal sites to be scored, e.g. to revise the score attributed to a previously examined skeletal site.

To achieve optimal matching performance, the reference images are preferably also subjected to multi scale processing (identical processing conditions as those applied to the ROI) so as to enable comparison under identical image quality conditions between reference pictures and the processed ROI.

A zooming functionality, to magnify the ROI (and corresponding reference images) may be implemented to achieve better visibility of small details, such as e.g. the corner of the epiphyses when it is believed to cap the metaphysics (bone age scoring) or to assess the presence or absence of an erosion (RA).

In this way a drawback of the conventional atlas-based method is overcome, namely that in the conventional atlas-based method the illustrations are small, implying that it difficult to observe e.g. the erosive and joint space abnormalities characterizing the different stages of rheumatoid arthritis.

ROI-specific processing is generally better than first globally optimizing the image quality of the entire image and next cutting out the ROI's. By first cutting out the ROI's from the unprocessed images and next subjecting them to image enhancement, the ROI image quality is higher because the image statistics used in the enhancement procedure are based on pixels of the ROI only.

Evidently, such stage-specific processing is impossible with the prior art using film images. Furthermore, it will be clear that the conventional atlas-based comparison method as used in the prior art is unable to provide the aforementioned improved functionalities.

The invention claimed is:

1. A method of radiographic scoring of a radiographic image comprising the steps of:

acquiring a digital image representation of an image to be subjected to radiographic scoring, applying the acquired image representation to a display device and generating a displayed image, determining and extracting at least one region of interest on the displayed image, retrieving for each said at least one extracted region of interest a corresponding region of interest in reference stage images from a database, each said reference stage image having an associated score number, displaying the extracted regions of interest from the displayed image and the corresponding reference regions of interest from said reference stage images in juxtaposition on the same display screen, selecting a displayed optimal region of interest within said reference regions of interest which most optimally matches with the extracted region of interest from said displayed image, associating with the region of interest from the displayed image a score number corresponding with the selected region of interest from the reference stage images, and combining score numbers associated with said regions of interest into an overall score number pertaining to said radiographic image.

2. A method according to claim 1 wherein the displayed reference stage image which most optimally matches with the displayed region of interest is selected by:
   displaying each said region of interest and the reference stage images pertaining to the displayed region of interest in close proximity to each other, and
   visually comparing the displayed region of interest and the displayed reference stage images pertaining to the displayed region of interest, and
   selecting the displayed reference image which visually most optimally matches with the displayed region of interest.

3. A method according to claim 1 wherein the step of determining the region of interest is guided by means of a stencil consisting of a sketch of a body part to be evaluated depicting at least one of the outline of the body part, bone contours and anatomical contours within said body part, in addition to region of interest delineations superimposed on said sketch.

4. A method according to claim 1 wherein a digital image representation of the region of interest is extracted from a digital image representation of said image by resampling and interpolation.

5. A method according to claim 3 wherein said stencil is selected on the basis of identification data such as gender, age, examination type.

6. A method according to claim 3 wherein the region of interest comprising a body part in said stencil, said region of interest being defined by said region of interest delineations, is mapped onto an actual position of the body part within an image to be scored.

7. A method according to claim 1 wherein data within the region of interest is subjected to image processing.

8. A method according to claim 1 wherein the reference stage image is subjected to image processing.

9. A method according to claim 7 wherein said image processing comprises a spatial reformatting process.

10. A method according to claim 8 wherein said image processing comprises a spatial reformatting process.

11. A method according to claim 7 wherein said image processing is an image enhancement process.

12. A method according to claim 8 wherein said image processing is an image enhancement process.

13. A computer readable medium encoded with a computer program adapted to carry out the following steps when run on a computer:
   displaying a radiographic image on a display device connected to said computer so as to generate a displayed image,
   upon indication by an operator of a region of interest in said displayed image, selecting and extracting said region of interest, and displaying said extracted region of interest on a display device,
   retrieving for a selected region of interest reference stage images from a database accessible via said computer, each of said reference stage images having an associated score number, displaying the retrieved reference stage images in juxtaposition with the said extracted region of interest on the same display device,
   selecting a displayed reference stage image which optimally matches with a displayed region of interest, associating with the displayed region of interest a score number which corresponds with the selected reference stage image,
   combining score numbers associated with said regions of interest into an overall score number pertaining to said radiographic image.

14. A computer readable medium encoded with a computer program according to claim 13 wherein a digital image representation of a region of interest is extracted from a digital image representation of said image by re-sampling and interpolation.

15. A computer readable medium encoded with a computer program according to claim 13 wherein a displayed reference stage image which most optimally matches with a displayed region of interest is selected by:
   displaying each of said regions of interest and the reference stage images pertaining to the displayed region of interest in close proximity to each other,
   visually comparing a displayed region of interest and displayed reference stage images pertaining to the displayed region of interest, and
   selecting a displayed reference image which visually most optimally matches with a displayed region of interest.

16. A computer readable medium encoded with a computer program according to claim 13 wherein the determining of a region of interest is guided by means of a stencil consisting of a sketch of a body part to be evaluated depicting at least one of the outline of the body part, bone contours and anatomical contours within said body part and region of interest delineations superimposed on said sketch.

17. A computer readable medium encoded with a computer program according to claim 13 wherein a region of interest comprising a body part in said stencil, said region of interest being defined by said region of interest delineations, is mapped onto the actual position of that body part within an image to be scored.

18. A computer readable medium encoded with a computer program according to claim 13 wherein data within a region of interest are subjected to image processing.

19. A computer readable medium encoded with a computer program according to claim 13 wherein a reference stage image is subjected to image processing.

20. A computer readable medium encoded with a computer program according to claim 13 wherein said image processing comprises a spatial reformatting process.

21. A computer readable medium encoded with a computer program according to claim 17 wherein said image processing is an image enhancement process.

22. A computer readable medium encoded with a computer program according to claim 18 wherein said image processing is an image enhancement process.

* * * * *